United States Patent [19]

Deutsch

[11] 4,224,455
[45] Sep. 23, 1980

[54] SULFONATED ALKOXYLATED ALKYL ARYLOL MALEATE REACTIVE SURFACTANTS

[75] Inventor: Julius H. Deutsch, Chicago, Ill.

[73] Assignee: Stepan Chemical Company, Northfield, Ill.

[21] Appl. No.: 959,419

[22] Filed: Nov. 13, 1978

Related U.S. Application Data

[63] Continuation-in-part of Ser. No. 831,176, Sep. 7, 1977, abandoned.

[51] Int. Cl.$^2$ .................... C07C 69/60; C07C 143/38
[52] U.S. Cl. .................................. 560/193; 526/209; 526/287; 560/194
[58] Field of Search ............................... 560/193, 194

[56] References Cited

U.S. PATENT DOCUMENTS

| | | | |
|---|---|---|---|
| 3,147,301 | 9/1964 | Sheetz | 560/193 |
| 3,169,142 | 2/1965 | Knaggs et al. | 260/458 R |
| 4,075,411 | 2/1978 | Dickstein | 560/193 |

FOREIGN PATENT DOCUMENTS 48-1712   1/1973   Japan ...................................... 560/193

*Primary Examiner*—Jane S. Myers
*Attorney, Agent, or Firm*—Hill, Van Santen, Steadman, Chiara & Simpson

[57]   ABSTRACT

New reactive surfactants or emulsifiers useful in a broad range of emulsion polymerization processes are provided, along with processes for making and using such. The reactive surfactants are comprised of ring sulfonated half esters of maleic anhydride with alkoxylated alkyl arylols.

6 Claims, No Drawings

SULFONATED ALKOXYLATED ALKYL ARYLOL MALEATE REACTIVE SURFACTANTS

RELATED APPLICATION

This application is a continuation-in-part of my earlier filed U.S. patent application Ser. No. 831,176, filed Sept. 7, 1977, now abandoned.

BACKGROUND OF THE INVENTION

In emulsion polymerization, non-copolymerizable surfactants (or emulsifiers) have been conventionally employed to emulsify reactants. While functional monomers, such as, for example, reactive carboxylic acids, like acrylic acid, sodium styrene sulfonate, 2-sulfoethyl methacrylate, and the like, have heretofore been used to impart stability to polymers made by emulsion polymerization, such monomers are not of themselves emulsifiers, and they contribute stability to a product polymer only after becoming part of the growing polymer molecule in a polymerization reaction. Such monomers must usually be used in an emulsion polymerization reaction in the presence of relatively large amounts of non-copolymerizable surfactants, which can itself be undesirable. In the art of producing stable and useful free radical induced polymers dispersed in water performed surfactants are employed for the intended purpose of emulsion polymerization. The surfactants heretofore in common use apparently do not become chemically reacted into a product polymer molecule by carbon to carbon bonding (as distinct from some sort of physical mixing, adsorbing, or the like).

Surfactants containing sulfonate groups are, of course, known, but, so far as now known to me, these materials are apparently not chemically reactive so as to be incorporatable by emulsion polymerization directly into an emulsion polymerized product because of inherent molecular structural considerations. The art seems to have experienced problems in introducing into a maleate having true surfactant properties both a sulfonate (as distinct from a sulfate) group and a reactive ethylenic double bond. Problems have also been experienced in the art in preparing such reactive surfactant molecules in a concentrated, long-term shelf-stable form such as would be necessary, or desirable, for example, for many commercial scale emulsion polymerization reactions wherein such reactive surfactants would be useful.

BRIEF SUMMARY OF THE INVENTION

The invention provides a class of ring sulfonated half esters of maleic anhydride and alkoxylated alkyl arylols which surprisingly not only are true anionic emulsifiers (surfactants), but also are reactive functional monomers which are copolymerizable under emulsion polymerization conditions. Such class of sulfonated esters displays an extremely broad range of applications in emulsion polymerization, depending upon the wishes of the user, and such class of reactive surfactants appears to overcome many of the above indicated limitations and disadvantages associated with prior art surfactants and functional monomers employed in emulsion polymerization.

In one aspect, this invention is directed to processes for making reactive sulfonated ester surfactants involving esterifying maleic anhydride with alkoxylated alkyl arylol, and then sulfonating the resulting product.

In another aspect, this invention is directed to reactive surfactants containing a nuclear sulfonate group and also a reactive ethylenic double bond which surfactants are polymerizable by free radical mechanisms.

Other and further aspects, aims, purposes, features, advantages, properties and the like will be apparent to those skilled in the art from the present specification.

DETAILED DESCRIPTION OF THE PREFERRED EMBODIMENTS

To make a reactive sulfonated ester surfactant of this invention, one, as a first step, forms a half ester reaction product from maleic anhydride and an alkoxylated arylol. Thus, one incrementally admixes at least one alkoxylated arylol with maleic anhydride while maintaining the reactive mixture at a temperature in the range of from about 20° to 110° C. (more preferably in the range of about 75° to 95° C.) and allows the reaction to proceed to produce a desired reaction product. Preferably, this reaction is conducted in the absence of water to avoid formation of maleic acid because the anhydride esterifies readily and completely with the arylol.

The reaction between maleic anhydride and alkoxylated arylol is characteristically exothermic, and the exotherm is controlled to within the temperature ranges above indicated by external heat removal (as with a cooling medium in a heat exchange relationship with such mixture). Before the subsequent sulfonation, it is preferred to remove any water present from such a reaction product by vacuum distillation or the like, but, when the preferred anhydrous reaction mixture is employed, usually no water is present since only the maleic half ester is being formed by regulating the mole ratio of maleic anhydride to alkoxylated arylol.

The starting alkoxylated arylols employed in the present invention are characterized by having incorporated thereinto from about 2 to 50 mols of at least one alkylene oxide material per mol of alkoxylated arylol, preferably from about 4 to 20 mols, and more preferably from about 5 to 10 mols, though larger and smaller quantities can be used, if desired. The alkylene oxide material thus incorporated into such an alkoxylated starting compound is selected from the group consisting of ethylene oxide (preferred), propylene oxide, and mixtures thereof. Thus, suitable alkoxylated arylol starting materials are characterized by the formula

$$HO-(R_1O)_n-A-R_2 \qquad (1)$$

where

R$_1$ is selected from the group consisting of ethylene, propylene, and mixtures thereof, R$_2$ is selected from the group consisting of hydrogen and alkyl groups each of which contains from and including 6 through 18 carbon atoms each, A is selected from the group consisting of substituted phenyl nucleii and substituted naphthyl nucleii, and n is a positive number of from about 2 through 50 inclusive, provided that, when R$_2$ is hydrogen, R$_1$O$_n$ has at least one of the following structures

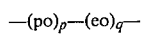

$$-(po)_p-(eo)_q-$$

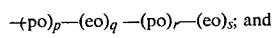

$$-(po)_p-(eo)_q-(po)_r-(eo)_s;\text{ and}$$

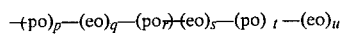

$$-(po)_p-(eo)_q-(po)_r-(eo)_s-(po)_t-(eo)_u$$

wherein p, r, and t, when present, are each an independently selected positive number of from about 3 through 9, inclusive, q, s, and u, when present, are each an independently selected positive number of from about 1 through 4, inclusive, and when the associated (eo) entity is a terminal block, q, s, and n can each be an independently selected positive number of from 1 through 20, P is propylene, and E is ethylene.

The term "substituted" as used herein in reference to "phenyl nucleii" and "naphthyl nucleii" is used to indicate that such nucleii are substituted by $R_2$ and $HO(R_1O)_n$ in formula (1) and in the formulas below shown, and such nucleii are not substituted by other moieties.

In Formula (1), A is preferably a substituted phenyl nucleus, and, when $R_2$ is an alkyl group and A is a substituted phenyl nucleus, $R_2$ contains from about 8 to 18 carbon atoms in each alkyl group thereof. A preferred class of formula (I) compounds comprises polyalkoxylated monoalkyl phenols and polyalkoxylated phenols (such as are produced by condensing alkylene oxide with monoalkyl phenol or phenol); some compounds within this class are available commercially under the trade designation "Makon" from Stepan Chemical Company, Northfield, Ill. Such preferred alkoxylated alkyl phenols typically are mixtures of ortho-alkyl substituted and para alkyl substituted phenols owing to the method of commercially alkylating phenol to produce the starting alkyl phenols used for subsequent reaction with alkylene oxides to make alkoxylated alkyl phenols. "Terminal" here references remoteness from A.

The incremental mixing of alkoxylated arylol with maleic anhydride in the practice of this invention is preferably adjusted so that the combined mole ratio of maleic anhydride to alkoxylated arylol reaches, in a reaction mixture, a range of from about 1:0.5 to 1:1 (based on starting materials). More preferably, such combined mole ratio of maleic anhydride to alkoxylated arylol is maintained at about 1:1.

When $R_2$ is alkyl in formula (1) preferably the alkyl group includes from about 8 to 14 carbon atoms. A particularly presently preferred alkoxylated alkyl arylol comprises an ethoxylated nonyl phenol which contains about 6 mols of ethylene oxide incorporated herein. Compounds of formula (1) are made by conventional procedures known to the prior art.

Conveniently, the incremental mixing of alkoxylated arylol with maleic anhydride is accomplished in a time interval ranging about 2-½ to 3-½ hours, although longer and shorter time intervals may be employed, as those skilled in the art will readily appreciate.

The resulting maleate half ester reaction product is then sulfonated with sulfur trioxide by any convenient procedure. Sulfonation is here preferably accomplished by contacting such a water-free half ester reaction product at a temperature below about 190° C. in the form of a thin liquid film with gaseous sulfur trioxide diluted with about 95 to 99% air or inert gas (such as nitrogen, argon, etc.). Preferably, the contact rate is from about 1:1 to 1:1.1 mole ratio of $SO_3$ to the half ester reaction product so that the equivalent of one sulfur trioxide molecule can be reacted with each molecule of the starting material (the half ester). When such acidified reaction product is of the 6 mole adduct of (eo), for example it has an acidity of at least about 1.8 milliequivalents per gram (meq/gm), though the acidity preferably can range from about 3 to 3.5 meq/gm due to carboxylic plus sulphonic acid groups. Usually, the meq/gm is below about 4. For purposes of the present invention, acidity of a sulfonated reaction product so produced is conveniently determinable by neutralizing with 0.1N KOH using phenolphthalein indicator to end point. The KOH neutralizes both the sulfonate hydrogen and the carboxylate hydrogen. Preferably, the thin film continuous sulfonation procedure described in U.S. Pat. No. 3,169,142 (the disclosure which is incorporated herein by reference) is employed.

Alternatively, one can sulfonate by contacting such a half ester with a dioxane/$SO_3$ complex (such as one made by dissolving $SO_3$ in ethylene dichloride and then mixing this solution with dioxane so as to produce a mole ratio of $SO_3$ to dioxane ranging from about 1:1 to 2:1), or with a tributyl phosphate/$SO_3$ complex (similarly prepared). Such a complex is mixed slowly with such reaction product while preferably maintaining the system below ambient temperatures.

A resulting sulfonated reaction product can, if desired, be neutralized with aqueous base (preferably alkali metal hydroxide or ammonium hydroxide, although amines, such as lower alkyl amines, lower alkanol amines, and tertiary amine compounds containing lower alkyl groups can be employed, if desired). Lower monoalkyl and lower dialkyl amines are presently preferred. As used herein, the term "lower" refers to a radical, such as an alkyl radical, containing less than 7 carbon atoms.

Reacting maleic anhydride with an alkoxylated arylol produces, as a primary product, a half ester, as indicated above, and the subsequent sulfonation surprisingly proceeds, preferably and primarily, nuclearly on the aromatic ring without adding to the terminal side chain reactive double bond (derived originally from the maleic anhydride).

A reaction product produced by such a process sequence as above described is preferably mixed with water to produce an aqueous system (which can be a solution, dispersion, or the like). The reaction product itself comprises an esterified product of maleic anhydride with alkoxylated arylol which is nuclearly substituted with at least one sulfonate group ($SO_3$) per molecule. Such product displays true surfactant activity, contains a reactive ethylenic double bond, and is polymerizable by free radical-type mechanisms with monomers of the type employed in emulsion polymerization processes.

The surfactant activity of a reaction product of this invention is characteristically at least sufficient to permit emulsion polymerization to be carried without the presence of non-reactive (in relation to a growing polymer chain), conventional-type surfactants, if desired.

The nuclearly sulfonated phenoxy poly (alkoxylene) oxy maleate products of this invention are characterized by the formula

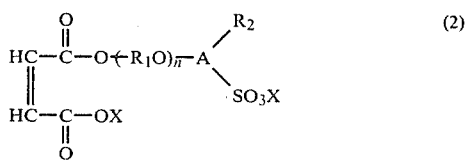
(2)

where
- $R_1$ is selected from the group consisting of ethylene, propylene, and mixtures thereof,
- $R_2$ is selected from the group consisting of hydrogen and alkyl groups each of which contains from 6 through 18 carbon atoms each,
- A is selected from the group consisting of phenyl nucleii or substituted phenyl nucleii and naphthyl nucleii or substituted naphthyl nucleii,
- X is selected from the group consisting of hydrogen, alkali metals, ammonium, lower monoalkyl amines lower dialkyl amines, lower trialkyl amines, lower monoalkanol amines, lower dialkanol amines, lower trialkanol amines, heterocyclic amines, phosphates, and mixtures thereof, and
- n is a positive number of from about 2 through 50 inclusive, provided that, when $R_2$ is hydrogen $(R_1O)_n$ has at least one of the following structures

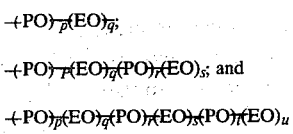

wherein
- p, r, and t, when present are each an independently selected positive number of from about 3 through 9, inclusive,
- q, s, and n, when present, are each an independently selected positive number of from about 1 through 4 inclusive, and when the associated (EO) entity is a terminated block, q,s, and a can each be an independently selected position number of from 1 to 20,
- P is propylene, and
- E is ethylene.

In formula (2), as in formula (1), A is preferably a phenyl nucleus, and when $R_2$ is an alkyl group and A is a phenyl nucleus, $R_2$ contains from about 8 to 18 carbon atoms in each alkyl group thereof.

A presently preferred class of formula (2) compounds comprises those wherein $R_2$ is alkyl, and X is selected from the class consisting of hydrogen, alkali metals, and ammonium. Such compounds are represented by the formula:

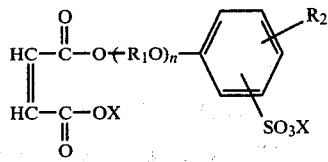

wherein:
- $R_1$ is selected from the group consisting of ethylene, propylene, and mixtures thereof,
- $R_2$ is an alkyl group consisting from about 8 to 18 carbon atoms,
- X is selected from the group consisting of hydrogen, alkali metals and ammonium,
- n is a positive whole number ranging from about 2 to 50.

As indicated above, owing to the common method of making monoalkyl substituted phenols, the location of $R_2$ is typically either ortho or para relative to $(R_1O)_n$. The location in any given compound of formula (3) of the $SO_3X$ group is not now known with certainty. Typically, compounds of formula (3) are mixtures of different ring sulfonated maleate half esters with one particular type of such sulfonate predominating.

Presently preferred compounds of formula (3) are those wherein X is hydrogen, $R_1$ is ethylene, and n ranges from about 4 through 12, inclusive.

As can be ascertained from the above formulas, esters resulting from the above described sequence of process steps in which maleic anhydride is reacted with alkoxylated arylols are, essentially, monoesters (or half esters) which are then sulfonated. The sulfonated product can be used in an acid form, or in a salt form, with such a salt form preferably being the alkali metal or ammonium salts thereof. Preferred alkali metals are sodium and potassium.

Neutralization of a sulfonation product with alkali metal hydroxides, ammonia and/or organic amines is readily and simply accomplished, preferably using aqueous solutions of such bases. Thus, one can produce clear solutions of acidic compounds of formula (2) containing from about 30 to 40 weight percent (35% weight being presently most preferred) acid esters with the balance, up to 100 weight percent, of any given product solution comprising water. Such solutions characteristically tend to remain clear, unless supersaturated, or unless excessively cooled (e.g. to temperatures below about 10° C.) Such a solution is then conveniently neutralized through addition thereto of aqueous base or preferably by addition of the acid to the base to form salts of formula (2) compounds or, preferably by addition of the acid to the base.

Examples of suitable amines for neutralization include lower alkyl amines (including mono-di-, and tri alkyl amines). A preferred such amine is selected from the group consisting of ethyl, diethyl, and triethyl amines, and mixtures thereof. The corresponding lower alkanol amines can also be advantageously employed. Heterocyclic amines, such as morpholine, pyridine, and the like, containing from 6 to 10 carbon atoms per molecule, can be used also in forming salts.

Reactive surfactants of this invention when in aqueous solution should preferably be stored at a pH below about 7 since certain reactive surfactants of this invention can hydrolyze at the ester linkage, particularly at high basic pH's. Ammonium, and amine salts, and the sulfonic acid products, presently appear to have longer shelf lives then some salts incorporating stronger cations. In general, the most stable of the products of formula (2) presently are believed to be those neutralized with mild alkali metal carbonates, ammonia, or disodium phosphate. Such a product can be prepared, for example, for first admixing and diluting a sulfonated reaction product with water, and then neutralizing the resulting system by adding an alkali metal carbonate, ammonium hydroxide, or amine thereto.

The true surfactant activity associated with the reactive surfactant products of the invention can be demonstrated by various procedures. For example, surface tension measurements of aqueous solutions show levels comparable to those of known materials displaying high surfactant activity. Also, for example, such products characteristically display a critical micelle concentration in aqueous media in the region which demonstrates their suitability for use in emulsion polymerization of highly efficient normally used non-reactive surfactants.

Products of the present invention are useful in emulsion polymerization, particularly in emulsion polymerization processes of the liquid phase type wherein water comprises the continuous phase, wherein initially liquid, pre-chosen, monomer material is present substantially as a dispersed phase at the initiation of polymerization. The liquid phase has incorporated therein a sufficient quantity of such sulfonated maleate reactive surfactant material of this invention to make a stable, small particle size, dispersed monomer phase. A sufficient quantity of a polymerization initiator is introduced (such as a conventional free radical initiator) to cause polymerization of the monomer materials at the particular temperatures employed. Conveniently, the quantity of such reactive surfactant so employed when used as the sole emulsion polymerization surfactant (preferred) can range from about 0.1 to 10 weight percent, based on the total monomer material content employed in a given emulsion polymerization system. Preferably, the amount of such reactive surfactant material employed ranges from about 0.5 to 3 weight percent similarly based on total monomer.

Characteristically, the polymer emulsions produced by incorporating thereinto a reactive surfactant of this invention are presently believed to have higher surface tensions for aqueous polymer emulsions (measured, for example, in dynes per centimeter at 25° C. with DeNuoy Tensiometer) that the same corresponding polymer emulsions made with conventional prior art surfactants (whether sulfonated or not). Evidently, such surface tension increase is caused by the incorporation of the starting reactive surfactant into a product polymer chemical structure through reaction of the reactive ethylenic double bonds thereof in such polymerization with an associated loss of surfactant activity. Such high surface tension characteristics make the product polymer emulsions have properties suitable for applications in areas where conventional surfactant-emulsion polymerized polymers are now employed.

Characteristically, the emulsion polymers produced using a reactive surfactant of this invention requires less surfactant in terms of percent or ratio on monomer weight than the total amount of prior art non reactive surfactant conventionally used in prior art emulsion polymerization. This is a particularly surprising phenomenon because the reactive surfactants of this invention have a relatively high molecular weight compared to conventional anionic surfactants used in emulsion polymerization, which means that the mole ratio of surfactant to monomer is characteristically even lower by the present invention than in prior art emulsion polymerization.

The reactive surfactants of this invention can be used in an emulsion polymerization reaction in combination with conventional emulsion polymerization surfactants, which can sometimes be useful, as when one desires to improve system stability characteristics, or to lower the costs of total surfactant used in a given situation. However, the reactive surfactants of this invention themselves characteristically display excellent capacity for producing superior emulsion stability characteristics in emulsion polymerization.

The reactive surfactants used in this invention, because of their characteristic and unusual stability towards polyvalent ions, can be used for emulsion polymerization in accord with this invention in acidic aqueous polymerization media, and under such conditions high rates of polymerization of monomers can be achieved at emulsion polymerization conditions (e.g. elevated temperatures and presence of initiator).

Examples of monomers which can be emulsion polymerized using a reactive surfactant of formula (2) include vinyl acetates, acrylic monomers, methacrylic monomers, styrene, alkylene monomers, and like conventional monomers.

EMBODIMENTS

The present invention is further illustrated by reference to the following examples. Those skilled in the art will appreciate that other and further embodiments are obvious and within the spirit and scope of this invention from the teachings of these present Examples taken with the accompanying specification.

EXAMPLE 1

Preparation of sulfonated alkyl aryl polyether maleate:

Maleic anhydride (8 moles) is melted in a reaction flask containing a stirrer and heated to 75° C., and 8.8 moles of an anhydrous 6 mole ethylene oxide condensate with nonylphenol is gradually and incrementally added thereto over a 3 hour period. The nonyl phenol employed is obtainable from Rohm and Haas and is understood to contain on a 100 weight percent basis from about 90–95 weight percent of para mononoyl phenol, about 2 to 8 weight percent of orthononyl phenol with the residual balance to total up to 100 weight percent being unknown hydrocarbons which apparently can include polyalkylated phenol species. Exotherm is controlled to maintain the mixture temperature below 100° C. Analysis of the product shows a 98% conversion of a half-ester product is achieved. Available data suggests a main component of this product has the structure

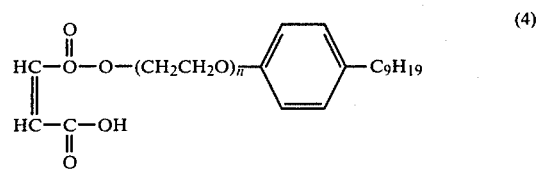 (4)

wherein n is about 6.

EXAMPLE 2

A portion of the half ester product of Example 1 is sulfonated with $SO_3$ vapor diluted with 98 weight percent air according to the thin film process procedure of Knaggs et al. U.S. Pat. No. 3,169,142 to an estimated $SO_3$/monoester mole ratio (combined) of 1:1. Acidity is carried to 3.32 meq/gm. Analysis of the resulting sulfonated product discloses that such is predominently nuclearly substituted with one sulfonic acid group per molecule. This product as recovered from such sulfonation is in the form of a light brown anhydrous liquid having an estimated viscosity of about 100,000 centipoises at 25° C.

Available data suggests that a main component of this product has the structure:

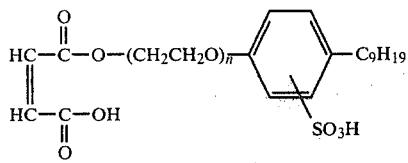

wherein n is about 6.

EXAMPLE 3

Part A

A portion of the product of Example 2 is dissolved in about 65 weight percent deionized water to produce a clear, stable solution having a highly acidic pH.

Part B

To the solution of Part A is added sufficient 10% by weight aqueous sodium hydroxide to produce a clear, transparent yellow solution having a pH of 7. Analysis reveals this neutralized product consists of 35 weight percent maleate ester actives (on a 100% total solution basis) and available data suggests that a main component of this product has the structure:

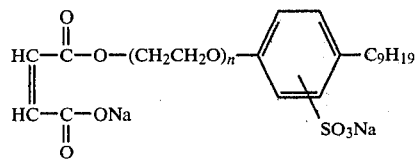

wherein n is about 6

In order to evaluate the surfactant capability of this sodium salt material, the following series of surface tension measurements are made using a DeNuoy Tensiometer and at the respective indicated solution concentrations in deionized water. Column A shows data developed using material from one batch of such material; column B shows data developed using material from another batch of such material, but made in a larger quantity (using the same relative proportions of starting agents):

TABLE I

| Concentrations gm/m. in D.I. Water | Col. A dynes/cm | Col. B dynes/cm |
|---|---|---|
| $2 \times 10^{-2}$ | 36.8 | 34.5 |
| $1 \times 10^{-2}$ | 34.2 | 34.6 |
| $5 \times 10^{-3}$ | 36.2 | 33.9 |
| $2 \times 10^{-3}$ | 35.6 | 33.9 |
| $1 \times 10^{-3}$ | 34.4 | 33.8 |
| $7 \times 10^{-4}$ | 32.2 | 31.2 |
| $5 \times 10^{-4}$ | 35.3 | 34.4 |
| $2 \times 10^{-4}$ | 36.5 | 36.0 |
| $1 \times 10^{-4}$ | 38.0 | 38.2 |
| $5 \times 10^{-5}$ | 41.8 | 42.2 |
| $1 \times 10^{-5}$ | 56.2 | 56.0 |

The CMC of both are around $7 \times 10$ gm/ml (CMC designates critical micelle concentration). This material is a unique emulsifier for emulsion polymerization. It is a reactive monomer. It is effective at very low concentrations. Being a sulfonate as opposed to a sulfate, it forms highly stable polymer emulsions at broad pH ranges. Surface tension of these polymer emulsions is usually very high; nevertheless, levelling is good. Adhesions to most surfaces is superior. This material is used to make all-acrylic polymers, styrene copolymers, vinyl acetate copolymers, and SBR and ABS systems. It is used as the sole emulsifier in ratios from 0.1% to 10% of monomer in aqueous emulsion polymerization.

Films cast from such polymer emulsions generally characteristically have the superior color stability to high temperatures expected of sulfonated surfactants over sulfated types.

The acid form of the Example 2 prepared as an aqueous solution as described in Example 3 can be used in place of this sodium salt form for emulsion polymerization with comparable, or in some cases superior results. For example, the sulfonic acid incorporated in the polymer chain acts as its own catalyst in certain cross linking reactions, is used.

The properties of the finished polymers can vary, not only when the cation is charged, but also when neutralization is carried out in situ or when the acid is used and the polymer neutralized on completion. The choice of exact emulsion polymerization procedure is believed to be not critical, except possibly where the un-neutralized (sulfonic acid form) product is used. In most cases, especially where a pre-prepared sodium salt is used, either high temperature (reflux) methods, or low temperature (redox) methods of emulsion polymerization are suitable, and pre-emulsion techniques are also suitable, as are stepwise addition methods of monomer or of pre-emulsion.

TABLE II

| | Properties Summarized | |
|---|---|---|
| | Sodium Salt | Sulfonic Acid |
| Actives: | 35% | 90-95% |
| Color: | yellow, clear liquid | reddish-brown, high viscosity liquid |
| Acidity: | | approx. 3.3 meq/gm |

EXAMPLE 4-7

This procedure of Examples 1 and 'b is repeated except that in place of the 6-mole ethoxylated nonyl phenol there is employed each of the following materials:

| Ex. No. | Starting alkoxylated alkyl phenol |
|---|---|
| 4 | ethoxylated nonyl phenol containing 4 moles of ethylene oxide |
| 5 | ethoxylated dodecyl phenol containing 12 moles of ethylene oxide |
| 6 | ethoxylated pentadecyl phenol containing 18 moles of ethylene oxide |
| 7 | block oligomer of ethylene oxide and propylene oxide substituted octyl phenol containing a total of 9 moles of such alkylene oxides but prepared by first adding 3 moles of propylene oxide followed immediately by 6 moles of ethylene oxide. |

EXAMPLES 8-15

The neutralization procedure of Example 3 is repeated except that in place of the product of Example 2 there is neutralized the following exemplary products using aqueous solutions of the salts indicated:

| Ex. No. | Product of Example No. | Base Used |
|---|---|---|
| 8 | 6 | ammonium hydroxide |
| 9 | 2 | potassium hydroxide |
| 10 | 5 | sodium methylate |
| 11 | 4 | disodium phosphate |
| 12 | 4 | sodium carbonate |

-continued

| Ex. No. | Product of Example No. | Base Used |
|---|---|---|
| 13 | 2 | diethyl amine |
| 14 | 2 | morpholine |
| 15 | 4 | diethanol amine |

EXAMPLE 16

Emulsion polymerization of acrylic copolymer using the product of Example 3:

(1) A mixture of 54 parts methyl methacrylate, 29.3 parts ethyl acrylate, 1.7 parts methacrylic acid, 0.7 parts of the product of Example 3 (dry weight basis), and 0.3 parts of ethoxylated nonyl phenol (containing about 6 moles ethylene oxide per mole) is emulsified in 45 parts water.

(2) Into a reaction flask are placed 55 parts water, 1 part of the product of Example 3 (dry weight basis), 0.25 parts $(NH_4)_2S_2O_8$, 9 parts methyl methacrylate, 5 parts ethyl acrylate and 0.3 parts methacrylic acid.

(3) A 1.0% solution of sodium hydrosulfite is used as an activator. This is added incrementally during the polymerization.

After initiating at 20° C. and reacting part (2) in an oxygen-free atmosphere, part (1) is added into the reactor over a one-hour period, maintaining a 10°-15° C. exotherm throughout. The finished polymer product resulted in a 98% yield (based on starting monomer). Results of analysis of the resulting polymer, neutralized to pH 8.4 with sodium hydroxide, are as follows:

Coagulum: 0.13% on solids
Solids: 44.5%
Viscosity: 17.5 cps.
Turbidity at 0.01%: 100 JTU *Jackson Turbidity Units)
Shear Stability (Waring Blender): Excellent
Freeze-Thaw Stability: Above 5 cycles
Polymer Emulsion Surface Tension (1%):53.5 d/cm at 25° C.

The surfactant of Example 3 is apparently chemically incorporated into the product polymer structure.

EXAMPLE 17

Using a 1.0 weight percent solution of sodium hydrosulfite as activator, and using a combination of 1 weight percent of the sulfonic acid derivative of Example 2 with 1 weight percent of the sodium salt of Example 3 (all based on total polymer solids), there is added to each of the following respective monomer mixtures in 100 parts by weight of water:

(a) 50 weight percent butyl acrylate, 25 weight percent methyl methacrylate, and 25 weight percent methacrylic acid (100 weight percent total monomer basis);

(b) 68 weight percent methyl methacrylate, 29 weight percent butyl acrylate, 3 weight percent acrylic acid, and 6 weight percent hydroxyethyl acrylate (100 weight percent total monomer basis); and (c) 45.5 weight percent methyl methacrylate, 50 weight percent ethyl acrylate, 2 weight percent hydroxyethyl acrylate, and 1.5 weight percent methacrylic acid.

Emulsion polymerization is conducted in an oxygen-free atmosphere for a period of one hour while maintaining a 10°-15° C. exotherm throughout. Finished polymer in each case resulted in a minimum yield of 98%.

EXAMPLE 18

Styrene Homopolymer 100 parts by weight water and 2 parts by weight of the surfactant product of Example 3 are placed into a reaction flask, together with 0.5 parts tert. butyl hydroperoxide. An emulsion is formed from 100 parts water, 1 part monomeric surfactant, and 0.5 part tert. butyl hydroperoxide. A 1.0% solution of sodium formaldehyde sulfoxylate is fed into the reactor. The styrene emulsion is fed into the reactor. The reaction temperature was raised to 70° C., after which monomer emulsion is fed into it, together with the sulfoxylate solution over a 1½ hour period.

| Polymer Product Analysis: | |
|---|---|
| Solids: | 44.68% |
| Viscosity: | 29 cps. |
| Coagul | 0.7% |
| Surface Tension: (1.0%) | 72 dynes/cm. |

The surfactant of Example 3 is chemically incorporated into the product polymer structure.

EXAMPLE 19

Styrene Copolymer 55 parts styrene, 40 parts butyl acrylate, 3 parts methacrylic acid, 2 parts monomeric surfactant of Example 3 reacted as in Example 18.

| Polymer Product analysis: | |
|---|---|
| Solids: | 49.4% |
| Viscosity: | 250 cps. |
| Shear Stability: | Excellent |
| Surface Tension (1%): | 59.5 dynes/cm |
| Coagulum: | 0.2% |

The surfactant of Example 3 is chemically incorporated into the product polymer structure.

EXAMPLE 20

Vinyl Acetate Homopolymer 100 parts vinyl acetate, 2 parts monomeric surfactant from Example 2, 2 parts polyvinyl alcohol (low mol. wt., 88% hydrolyzed, as in Borden 5-88), 0.2 parts $K_2S_2O_8$, 0.2 parts tert. butyl hydroperoxide, 0.03 parts $FeSO_4$, 0.2 parts sodium formaldehyde sulfoxylate as a 2% solution in water. Add 25 parts water, 40% of the monomer surfactant, all the $K_2S_2O_8$ and 25% of the vinyl acetate monomer to the reaction vessel. Heat to 40° C.

The rest of the water, monomer, monomer surfactant, polyvinyl alcohol, and tert. butyl hydroperoxide are mixed to form a pre-emulsion and prepared to add incrementally.

Upon addition of part of the sodium formaldehyde sulfoxylate and $FeSO_4$ to the initial reaction mix, a vigorous exotherm results, after which the pre-emulsion and the rest of the sodium formaldehyde sulfoxylate are added incrementally over a 1.5 hour period.

| Product Polymer Analysis: | |
|---|---|
| Solids: | 53.5% |

-continued

| Product Polymer Analysis: | |
|---|---|
| Viscosity: | 122 cps. at 25° C. |
| Turbidity: | 40 JTU |
| Surface Tension (1%) | 45.5 dynes/cm |

EXAMPLE 21 Styrene-Butadiene 57.7 parts styrene, 40 parts butadiene, 2.0 parts of monomeric surfactant of Example 3, 0.3 parts of an adduct of nonyl phenol containing about 6 mols ethylene oxide per mol of phenol. 0.2 parts dodecyl mercaptan, 0.2 parts $K_2S_2O_8$, $NaHPO_4$ to pH 7.0, 100 parts water, all are charged to a reactor pressure bottle. Product polymerized in such pressure bottle at 70° C. for 24 hours.

| Product Polymer Analysis: | |
|---|---|
| Solids: | 55.3% |
| No coagulum | |
| Excellent water spot resistance | |

As is apparent from the foregoing specification, the present invention is susceptible of being embodied with various alterations and modifications which may differ particularly from those that have been described in the preceding specification and description. For this reason, it is to be fully understood that all of the foregoing is intended to be merely illustrative and is not to be construed or interpreted as being restrictive or otherwise limiting of the present invention, excepting as it is set forth in the hereto-appended claims.

EXAMPLE 22

Vinyl Acetate Copolymer for General Coatings Cross-Linking

Monomers: Vinyl Acetate, Butyl Acrylate, N-Methylolacrylamide, Itaconic Acid
Est. Wt. Ratios: 73/20/5/2, product of Example 3
Recipe:

| | parts |
|---|---|
| 1. Water (D.I.) | 300.0 |
| 2. Product of Example 3 (34%) | 14.6 |
| 3. Itaconic Acid | 10.0 |
| 4. Mercaptoacetic Acid | 1.0 |
| 5. Tert. Butyl Hydroperoxide | 0.5 |
| 6. NaHPO4 | 1.5 |
| 7. Vinyl Acetate | 70.0 |
| 8. Butyl Acrylate | 25.0 |
| 9. Vinyl Acetate | 295.0 |
| 10. Butyl Acrylate | 75.0 |
| 11. Tert. Butyl Hydroperoxide | 1.0 |
| 12. N-Methyol acrylamide | 42.0 |
| 13. Product of Example 3 (34%) | 14.6 |
| 14. Water (D.I.) | 100.0 |
| 15. Sequestrene NaFe | 0.1 |
| 16. Sodium Formaldehyde Sulfoxylate (2%) | 100.0 |

Procedure:
1. Mix (1) through (8) in the reaction flask and purge with nitrogen.
2. Blend (9) through (14) to form a pre-emulsion and place into an additional funnel.
3. Heat flask to 35°–40° C. and add (15). Follow with addition of 10 cc (16). Allow to exotherm 10°–12° C. before starting addition to pre-emulsion together with incremental addition of (16).
4. When all monomer is in, add a few drops of (11) and heat to 5° C. above peak and hold to react residual monomer.
5. Adjust pH as desired and cool.

Results:

| Solids: | 43.5% |
|---|---|
| Viscosity: | 50 cps. |
| pH: | 4.0 |
| Coagulum: | Trace |
| Turbidity: | 110 JTU |
| Freeze-Thaw Stability: | 3+ cycles |
| Acid Stability: | Excellent |
| Salt Stability: | Excellent |
| Mechanical Stability: | Excellent |

Dried Film gives very good water spot and wet scrub resistance.

EXAMPLE 23

Sulfonic Acid of Acrylic Copolymer

Monomers: Methyl Methacrylate, Ethyl Acrylate Copolymer
Est. Wt. Ratios: 55/54
Example 2 product:
Recipe:

| | Parts |
|---|---|
| 1. Water (D.I.) | 260.0 |
| 2. Ethyl Acrylate | 30.0 |
| 3. Example 2 - Sulfonic Acid | 1.0 |
| 4. Mercaptoacetic Acid | 0.2 |
| 5. Tert. Butyl Hydroperoxide | 1.0 |
| 6. Sequestrene NaFe | 0.01 |
| 7. Sodium Formaldehyde Sulfoxylate (2%) | 50.0 |
| 8. Methyl Methacrylate | 165.0 |
| 9. Ethyl Acrylate | 105.0 |
| 10. Example 2 - Sulfonic Acid | 1.0 |
| 11. Tert. Butyl Hydroperoxide | 1.0 |

Procedure:
1. Add (1), (3), and (4) to flask with agitation. Dissolve (5) in (2) and add over a five minute period. Mix ten minutes.
2. Add (6) and follow with gradual addition of (7).
3. Blend (8), (9), and (11) for feeding into the reactor.
4. Dissolve (10) in 30 cc water for feed into reactor.
5. Allow (2) to react completely to form a seed for the rest of the monomer.
6. When all of (2) has reacted, start drop-wise addition of (10). After 2 cc have been added, start adding monomer slowly at first. Add (7) concurrently.

Results:

| Solids: | 42% |
|---|---|
| Coagulum: | 0.1% |
| pH: | 2.2 |

If a higher ethyl acrylate copolymer is desired, form seed with ethyl acrylate rather than methyl methacrylate.

EXAMPLE 24

Methyl Methacrylate—Ethyl Acrylate Copolymers For Paints or Paper Coatings Made With Example 8 Product The following copolymer is made with 1.5% of the ammonium salt made in situ from Example 8 sulfonic acid. About 0.3% nonionic surfactant, such as a 4 mole ethoxylate of nonyl phenol, if a 4 mole ethoxylate of nonyl phenol post-added, will improve mechanical and polyvalent ion stability. The sodium salt of Example 3 is also an excellent stabilizer. Adhesion and scrub resistance of the polymer are superior.

| Recipe: | Parts |
| --- | --- |
| 1. Water (D.I.) | 390.0 |
| 2. Ammonia (28%) | 2.5 |
| 3. Example 2 Product | 7.5 |
| 4. $(NH_4)_2 CO_3$ | 0.9 |
| 5. Methacrylic Acid | 2.5 |
| 6. Methyl Methacrylate | 20.0 |
| 7. Ethyl Acrylate | 30.0 |
| 8. $BrCCl_3$ | 1.0 |
| 9. Tert. Butyl Hydroperoxide | 1.0 |
| 10. Methyl Methacrylate | 180.0 |
| 11. Ethyl Acrylate | 270.0 |
| 12. Sodium Formaldehyde Sulfoxylate (1%) | 50.0 |
| 13. Tert. Butyl Hydroperoxide | 1.0 |
| 14. $(NH_4)_2 CO_3$ | 0.5 |

Procedure:
1. Add (1) and (2) to the reactor and flush with nitrogen. Add (3) slowly. (Note: Dilute with 30 to 40 drops of 3A ethanol to make flowable.) Add (4).
2. Blend (5), (6), and (8) and add to the reactor slowly. pH=5.0. Flush with nitrogen.
3. Blend (9), (10), and (11), flush with nitrogen and place into an addition funnel.
4. Dissolve (14) in (12), flusk and place into an addition funnel.
5. Add (13) to the reaction flask, and with batch temperature at 20° C., start adding activator [(12) and (14)]. Allow to exotherm 6° C. to 8° C.; then start adding the monomer blend.
6. Total addition time is approximately two hours. Activator and monomers should be added at a rate to permit completion of both at the same time. Exotherm averages 10°-12° C. throughout. Maximum batch temperature reached is approximately 40° C.
7. Heat batch to maximum of peak, and hold to completion. Cool and adjust with desired alkali.

Results:

| pH adjusted to 9.0 with ammonia. | |
| --- | --- |
| Solids: | 50% |
| Coagulum: | 0.19% |
| Surface Tension (1%): | 49.3 d/cm |
| Viscosity: | 36 cps. |
| Turbidity: | 160 JTU |

EXAMPLE 25

Vinyl Acetate Copolymers Cross-Linking Type For Paints

Monomers: Vinyl Acetate, 2-Ethylhexyl Acrylate, N-Methylolacrylamide, Acrylic Acid
Est. Wt. Ratios: 76/17/5/2, Example 3, 1%

Recipe:

| | Parts |
| --- | --- |
| 1. Water (D.I.) | 200.0 |
| 2. (34%) Example 3 | 10.0 |
| 3. $K_2S_2O_8$ | 2.0 |
| 4. $NaHCO_3$ | 1.0 |
| 5. Dodecyl Mercaptan | 1.0 |
| 6. Acrylic Acid | 2.0 |
| 7. 2-Ethylhexyl Acrylate | 25.0 |
| 8. Vinyl Acetate | 80.0 |
| 9. (34%) Example 3 | 4.6 |
| 10. Water (D.I.) | 200.0 |
| 11. 2-Ethylhexyl Acrylate | 60.0 |
| 12. N-Methylolacrylamide (60%) | 42.0 |
| 13. Acrylic Acid | 8.0 |
| 14. Vinyl Acetate | 300.0 |
| 15. $NaHCO_3$ | 2.0 |
| 16. Sequestrene NaFe | 0.2 |
| 17. Sodium Formaldehyde Sulfoxylate (2%) | 85.0 |

Procedure:
1. Add (1) through (8) to the reaction flask. Purge thoroughly with nitrogen. Maintain a nitrogen blanket over the reaction surface throughout the run.
2. Blend (9), (10), and (15). Purge with nitrogen. Blend (11), (12), (13), and (14), and add to form an emulsion while maintaining a nitrogen purge. Place into a feed funnel.
3. Place (17) into a separate feed funnel.
4. Heat batch to 15° C. and add (16).
5. Start addition of (17) and 10 drops of tert. butyl hydroperoxide. Allow to exotherm 15° C. (to 40°-48° C.).
6. Start adding pre-emulsion over a two hour period; concurrently adding (17). Maximum temperature is 45° C. When complete, heat to 50° C. and hold for complete reaction.

Note that additional increments of tert. butyl hydroperoxide may be required to maintain a high exotherm.

Results:

| Solids: | 45% |
| --- | --- |
| Viscosity: | 75 cps. |
| Coagulum: | 0.14% |
| Turbidity: | 115 JTU |
| Surface Tension (1%): | 43.5 d/cm |
| pH: | 4.3 |
| Polyvalent Ion Stability: | Excellent |
| Strong Acid Stability: | Excellent |
| Mechanical Stability: | Excellent |

EXAMPLE 26

Styrene Terpolymer

Preparation of Styrene, Ethyl Acrylate, Methacrylic Acid
Terpolymer
Est. Wt.
Ratios: 38.5/60.2/1.3, Example 8 product
Note: This terpolymer is used as the skeleton for making the graft polymer for the next recipe, 651-53B.

Recipe:

| | | Parts |
| --- | --- | --- |
| 1. | Water | 400.0 |
| 2. | Ammonium salt of Example 8 (34%) | 12.0 |
| 3. | Tert. Butyl Hydroperoxide | 4.0 |

-continued

|    |                      | Parts  |
|----|----------------------|--------|
| 4. | BrCCl$_3$            | 1.2    |
| 5. | Methacrylic Acid     | 6.0    |
| 6. | Ethyl Acrylate       | 74.0   |
| 7. | Water                | 160.0  |
| 8. | Ammon. salt of Ex. 2 | 4.2    |
| 9. | Tert. Butyl Hydroperoxide | 2.0 |
| 10.| Styrene              | 174.0  |
| 11.| Ethyl Acrylate       | 200.0  |
| 12.| BrCCl$_3$            | 1.2    |
| 13.| Sequestrene NaFe     | 0.04   |
| 14.| Formapon (2%)        | 115.0  |

Procedure:
1. Blend (1), (2), and (3) in the reaction vessel and purge with nitrogen.
2. Mix (4), (5), and (6) as Part A. Mix (7), (8), and (9) as Part B. Blend (10), (11), and (12) as Part C.
3. Adjust reactor blend to 23°–25° C. Add Part A. Mix well and then add (13). Follow drop-wise with (14). Allow to exotherm to peak. Then start simultaneous addition of Part B and Part C.
4. Maintain a good exotherm. Pause with addition of Part B at regular intervals to allow for complete reaction. Maintain as low a free monomer level as possible; in other words, avoid build-up.
5. After completing addition, allow for reaction of all residual monomer. Then cool to 20° C.

Results:

| Solids:               | 38.3%          |
|-----------------------|----------------|
| pH:                   | 2.6            |
| Coagulum:             | None           |
| Surface Tension (1%): | 50.8 dynes/cm  |
| Turbidity (0.01%):    | 180 JTU        |
| Mechanical Stability: | excellent      |

EXAMPLE 27

Graft Copolymer

This polymer is based on the styrene terpolymer of Example 26 recipe as the base, with grafting of additional styrene and acrylonitrile to give the following weight ratios (estimated): Styrene, Ethyl Acrylate, Acrylonitrile, Methacrylic Acid 45.3/45.2/8.5/1.0

Total Agent Ammonium salt of Example 8 for the polymer: 0.94%
Total Chain Transfer Agent: 0.4%

Recipe:

|    |                              | Parts  |
|----|------------------------------|--------|
| 1. | Styrene Terpolymer Base (38.3%) | 809.0 |
| 2. | Styrene                      | 64.4   |
| 3. | Acrylonitrile                | 35.0   |
| 4. | Tert. Butyl Hydroperoxide    | 1.35   |

Procedure:
With the styrene terpolymer base in the reaction vessel, add the blend of (2), (3) and (4) over an eight to ten minute period. A vigorous exotherm will develop almost immediately. Control to maintain temperature below 50° C. and allow to react to completion. After cooling, adjust pH with weak base.

Results:

| Solids: | 45% |
|---------|-----|

-continued

| Surface Tension (1%): | 48 dynes/cm |
|-----------------------|-------------|
| Turbidity (0.01%)     | 215 JTU     |
| Coagulation:          | None        |
| pH:                   | 9.0         |
| Mechanical Stability: | excellent   |

EXAMPLE 28

Cross-Linking Acrylic Copolymer

Monomers: Methyl Methacrylate, Butyl Acrylate, Methacrylic Acid, Hydroxypropyl Methacrylate
Estimated
Weight Ratios: 68.75/23/2.75/5.5, (Example 3) (34%)

Recipe:

|     |                                   | Parts  |
|-----|-----------------------------------|--------|
| 1.  | Water                             | 90.0   |
| 2.  | K$_2$S$_2$O$_8$                   | 0.3    |
| 3.  | (NH$_4$)$_2$CO$_3$                | 0.15   |
| 4.  | Tert. Butyl Hydroperoxide         | 0.05   |
| 5.  | Water                             | 150.0  |
| 6.  | Example 3 (34%)                   | 17.5   |
| 7.  | K$_2$S$_2$O$_8$                   | 1.2    |
| 8.  | (NH$_4$)$_2$CO$_3$                | 1.15   |
| 9.  | Methyl Methacrylate               | 225.0  |
| 10. | Butyl Acrylate                    | 75.0   |
| 11. | Acrylic Acid                      | 9.0    |
| 12. | Hydroxypropyl Methacryalate (94%) | 19.15  |
| 13. | Tert. Butyl Hydroperoxide         | 0.25   |
| 14. | Sodium Formaldehyde Sulfoxalate (2%) | 25.0 |
| 15. | Tert. Butyl Hydroperoxide         | 0.05   |

Procedure:
1. Blend (1), (2), (3), and (4) in the reactor. Purge thoroughly with nitrogen.
2. Blend one half of (5), (6), (7), (8), (9), (10), (13) and all of (11) to form a pre-emulsion feed.
3. Blend one half of (5), (6), (7), (8), (9), (10), (13) and all of (12) to form a second pre-emulsion feed.
4. Heat the solution in the reactor to 50° C. Then start addition of the first pre-emulsion and (14). Allow to exotherm, and maintain at about 10° C. above that of the bath throughout the addition.
5. When all emulsion I is in, allow to peak; heat to 70° C. for 15–20 minutes. Cool to 50° C. and start addition of the second pre-emulsion. Repeat procedure. When all residual monomer has reacted, cool and adjust.

Results:

| Solids:               | 54.5%                    |
|-----------------------|--------------------------|
| Viscosity:            | 50 cps                   |
| Turbidity (.01%)      | 150 JTU                  |
| Surface Tension (1%): | 54.5 dynes/cm            |
| Coagulum:             | 0.2%                     |
| Mechanical Stability: | Excellent (Waring Blender) |
| Freeze-Thaw Stability:| 5+ cycles                |

EXAMPLE 29

Cross Linking Type Of Acrylic Copolymers

Monomers: Methyl Methacrylate, Ethyl Acrylate, Hydroxyethyl Acrylate, Methacrylic Acid
Estimated
Weight Ratios: 46/50.5/2/1.5
Example 2–2%
Example 3–0.1%

Recipe:

|    |                            | Parts |
|----|----------------------------|-------|
| 1. | Water                      | 144.0 |
| 2. | Example 3 (34%)            | 0.25  |
| 3. | K$_2$S$_2$O$_8$            | 3.5   |
| 4. | Water                      | 179.0 |
| 5. | Example 3 - in water (34%) | 0.88  |
| 6. | Example 2 - in water (12%) | 62.5  |
| 7. | Hydroxyethyl Acrylate      | 7.5   |
| 8. | Methacrylic Acid           | 5.7   |
| 9. | Methyl Methacrylate        | 172.0 |
| 10.| Ethyl acrylate             | 190.0 |
| 11.| Tert. Dodecyl Mercaptan    | 3.8   |

Procedure:
1. Add (1) and (2) to the reaction flask.
2. Place (3), (4), and (5) into an addition funnel.
3. Place (7), (8), (9), (10), and (11) into a separate addition funnel.
4. Place (6) into a third addition funnel.
5. Heat batch to 85° C. and add 35 cc of (3), (4), and (5) blend. Allow reaction to start, and follow with concurrent addition of all flows.
6. When all flows are in, heat to complete the reaction.

Results:

| Solids:                | 50.3%                  |
|------------------------|------------------------|
| Viscosity:             | 17 cps.                |
| Turbidity:             | 120 JTU                |
| Freeze-Thaw Stability: | 5+ cycles              |
| Mechanical Stability:  | Excellent              |
| pH:                    | 8.0 (adjusted with NaOH) |

Adjust pH very carefully to avoid coagulation.
Excellent water spot and wet rub resistance.

EXAMPLE 30

Monomers: Styrene, Ethyl Acrylate, Acrylonitrile, Methacrylic Acid
Est. Wt. Ratios: 45.25/45.25/8.50/1 Surfactant 1% of Product of Example 8
Recipe:

|     |                                    | Parts |
|-----|------------------------------------|-------|
| 1.  | Water (D.I.)                       | 200.0 |
| 2.  | Example 8 (35%)                    | 6.0   |
| 3.  | Tert. Butyl Hydroperoxide          | 2.0   |
| 4.  | BrCCl$_3$                          | 0.6   |
| 5.  | Methacrylic Acid                   | 3.0   |
| 6.  | Ethyl Acrylate                     | 37.0  |
| 7.  | Water                              | 100.0 |
| 8.  | Example 8 (35%)                    | 2.6   |
| 9.  | Styrene                            | 87.0  |
| 10. | Ethyl Acrylate                     | 100.0 |
| 11. | Tert. Butyl Hydroperoxide          | 1.0   |
| 12. | BrCCl$_3$                          | 0.6   |
| 13. | Styrene                            | 50.0  |
| 14. | Acrylonitrile                      | 26.0  |
| 15. | Tert. Butyl Hydroperoxide          | 1.0   |
| 16. | Sequestrene NaFe                   | 0.02  |
| 17. | Sodium Formaldehyde Sulfoxylate (2%) | 60.0 |

The ammonium salt is made from Example 2 sulfonic acid. About 10% 3A alcohol is added to the acid to reduce viscosity after which a 3.5% solution of NH$_4$OH is added, to pH 7 to 8. Acidity of the sulfonic acid is 3.3 meq./gm. Add the ammonia solution slowly with good agitation, and holding temperature below 40° C. Buffer with (NH$_4$)$_2$CO$_3$ (0.3%)

Procedure:
1. Add (1), (2), and (3) to the reactor. Purge with Nitrogen.
2. Blend (4), (5), and (6) and add to the reactor. Mix 15 minutes.
3. Mix (7) and (8) and place into addition funnel A.
4. Blend (9), (10), (11), and (12) and place into addition funnel B.
5. Blend (13), (14), and (15) and place into addition funnel C.
6. Set batch temperature at 20° C. and maintain a 20° C. bath. Add (16), and follow with a drop-wise addition of (17), until there is a 8°-10° C. exotherm; start adding flows A and B slowly, maintaining at least an 8°-10° C. exotherm. It may be necessary to stop the addition 2 or 3 times so as to react all monomers.
7. When all of B and ½ of A have been added (about 2 hours), allow the temperature to peak. Hold at peak temperature for 1 hour, and cool to 20°-25° C.
8. Add all of flow C and all of remaining flow A over a 10 minute period. Product should immediately become exothermic. Allow to completely react by heating bath to peak of exotherm and hold at that temperature to completion.

Results:

| Solids:               | 45.2%        |
|-----------------------|--------------|
| coagulum:             | none         |
| pH:                   | 7.5          |
| Turbidity (0.01%):    | 230 JTU      |
| Surface Tension (1%): | 51.5 dynes/cm|
| Mechanical Stability: | excellent    |

EXAMPLE 31

Polymers of Styrene-Butadiene-Methacrylic Acid
Est. Weight Recipe:

|     |                          | A    | B    | C    | D       | E       |
|-----|--------------------------|------|------|------|---------|---------|
| 1.  | Styrene                  | 57.0 | 57.5 | 57.5 | 50.0    | 60      |
| 2.  | Butadiene                | 40.0 | 40.0 | 40.0 | 48.0    | 37.0    |
| 3.  | Methacrylic Acid         | 3.0  | —    | —    | —       | 3.0     |
| 4.  | Acrylic Acid             | —    | 2.5  | 2.5  | 2.0     | —       |
| 5.  | DDM                      | 0.02 | 0.02 | 0.02 | 0.02    | 0.2     |
| 6.  | Water                    | 67.0 | 67.0 | 67.0 | 100.0   | 80.0    |
| 7.  | TKPP (5%)                | 4.0  | 4.0  | 4.0  | 4.0     | 6.0     |
| 8.  | NaOH (10%) Example 3 (34%) | 8.3 | 8.3 | 8.3 | to pH 7 | to pH 6 |
| 9.  | Sulfonic Acid Example 2  | —    | —    | —    | —       | 0.75    |
| 10. | K$_2$S$_2$O$_8$ (4%)     | 8.3  | 8.3  | 8.3  | 8.3     | 10.0    |

Procedure:
All the above were bottle runs, made in an Atlas Launderometer. In A through D, water, Agent Example 3, Buffer and alkali were added to the bottle and flushed with nitrogen. Styrene and mercaptan are then added. Add K$_2$S$_2$O$_8$. Follow with butadiene and cap.

The bath temperature is set at 40° C., and add 0.002 grams dissolved Sequestrene NaFe to the bottles before mounting.

In recipe D, add the Agent, Example 2 acid to the water before neutralizing.

The batch is run one hour at 40°-45° C., after which the batch temperature is gradually increased over a six hour period, to 70° C. It is run at 70° C. for 24 hours.

All runs were free of coagulum, and had solids of 48-52 %, with viscosities below 500 cps.

EXAMPLE 32

Vinyl Acetate Terpolymer For Paints Crosslinking

Monomers: Vinyl Acetate, Butyl Acrylate, Hydroxyethyl Acrylate

Est. Wt.
Ratios: 75/22/3, Example 3, 0.5%.

Recipe:

|  | Parts |
|---|---|
| 1. Water (D.I.) | 500.0 |
| 2. Example 3 (34%) | 8.0 |
| 3. (NH4)2S2O8 | 2.0 |
| 4. Vinyl Acetate | 100.0 |
| 5. Butyl Acrylate | 65.0 |
| 6. Water | 50.0 |
| 7. Example 3 (34%) | 5.0 |
| 8. Vinyl Acetate | 463.0 |
| 9. Butyl Acrylate | 100.0 |
| 10. Hydroxyethyl Acrylate | 24.0 |
| 11. Sequestrene NaFe | 0.2 |
| 12. Sodium Formaldehyde Sulfoxylate (1%) | 90.0 |
| 13. Tert. Butyl Hydroperoxide | 2.0 |
| 14. NaHCO3 (6%) | 30.0 |

Procedure:
1. Mix (1), (2), and (3). Heat to 45°-50° C.
2. Blend (4) and (5) as part A. Blend (6) and (7) as part B. Blend (8), (9), (10), and (13) as part C. Flush all thoroughly with nitrogen gas.
3. When temperature of batch reaches 45° C., add (11), and start part A and (12). Use (14) to maintain pH 4-5. It will take approximately 20 minutes to add part A. There will be an exotherm of 8°-12° C. Allow to peak before starting addition of part C, concurrently with a solution of (6) and (7).
4. After all monomer and Example 3 have been added, raise temperature 5° C. and hold until all monomer has reacted. Cool to room temperature and adjust pH.

Results:

| Solids: | 49.5% |
|---|---|
| Viscosity: | 22.5 cps. |
| Turbidity: | 97 JTU |
| Surface Tension: | 50.3 d/cm |
| Coagulum: | 2% |

[Note: It is felt coagulum can be reduced by better distribution of hydroxy ethyl acrylate. This can be done by adding part of it with monomer blend (4) and (5).] Product should be post-stabilized with 0.2%-0.5% Polystep F-12.

EXAMPLE 33

Acrylic Copolymer

Monomers: Methyl Methacrylate, Ethyl Acrylate, Methacrylic Acid

Est. Wt. Ratios: 48.4/48.4/3.2, Example 3

Recipe:

|  | Parts |
|---|---|
| 1. Water (D.I.) | 585.0 |
| 2. Methacrylic Acid | 2.0 |
| 3. K2S2O8 | 2.0 |
| 4. Sequestrene NaFe | 0.1 |
| 5. Methyl Methacrylate | 225.0 |
| 6. Ethyl Acrylate | 225.0 |
| 7. Methacrylic Acid | 13.0 |
| 8. Example 3 (34%) | 40.0 |
| 9. Sodium Hydrosulfite (2%) | 33.0 |

Procedure:
1. Add (1), (2), (3) and (8) to the reactor. Flush thoroughly with nitrogen.
2. Blend (5), (6), and (7) and 75 cc to the reaction flask over a three minute period. Mix 5 minutes longer. Batch temperature is at 20°-25° C. p1 3. Add (4) and follow with drop-wise addition of (9).
4. Allow to exotherm 10°-12° C. and start addition of the monomer blend. Maintain a 10°-12° C. exotherm throughout the addition period of about one hour.
5. If necessary to work off residual monomer, raise to a maximum of 50° C. Then cool and adjust pH.

Results:

| Solids: | 43% |
|---|---|
| Viscosity: | 17.5 cps. |
| Mechanical Stability: | Excellent |
| pH: | 9.0 |
| Coagulation: | 0.04 |
| Freeze-Thaw Stability: | 5+ cycles |
| Turbidity: | 73 JTU |
| Surface Tension (1%): | 54.8 d/cm |

EXAMPLE 34

Styrene Homopolymer With 3% (Example 3)

Recipe:

| 1. Water (D.I.) | 100.0 |
|---|---|
| 2. Example 3 (34%) | 11.5 |
| 3. Water | 100.0 |
| 4. Example 3 (34%) | 5.8 |
| 5. Styrene | 200.0 |
| 6. Tert. Butyl Hydroperoxide | 1.0 |
| 7. Sodium Formaldehyde Sulfoxylate (1%) | 30.0 |

Procedure:
1. Add (1) and (2) to the reaction flask. Purge with nitrogen. Heat to 70° C. Add ⅓ of (5) and mix 15 minutes. Add ⅓ of (6).
2. Make a pre-emulsion of the remaining (5) and (6).
3. Start addition of (7) slowly. An exotherm develops. Allow to peak. Add as long as the exotherm continues. Then start adding pre-emulsion, until all monomer is in. The entire addition period is about one hour.
4. When all pre-emulsion is in, add a few drops of tert. butyl hydroperoxide and heat to 90° C. Hold to completion.

Results:

| Solids: | 45% |
|---|---|
| Viscosity: | 30 cps. |
| Turbidity (0.1%): | 180 JTU |
| Surface Tension: | 72 d/cm |

EXAMPLE 35

High Carboxylic Acid Acrylic Polymer

Monomers: Butyl Acrylate, Methyl Methacrylate, Methacrylic Acid

Est. Wt.
Ratios: 50/25/25
Example 3 (A) 1%, (B) 2%
Recipe:

|  | Parts | |
|---|---|---|
|  | A. | B. |
| 1. Water | 140.0 | 140.0 |
| 2. Tert. Butyl Hydroperoxide | 0.5 | 0.5 |
| 3. Butyl Acrylate | 150.0 | 150.0 |
| 4. Methyl Methacrylate | 75.0 | 75.0 |
| 5. Methacrylate Acid | 75.0 | 75.0 |
| 6. BrCCl$_3$ | 2.0 | 2.0 |
| 7. Example 3(34%) | 8.76 | 17.52 |
| 8. Water | 130.0 | 130.0 |
| 9. Sequestrene NaFe | 0.05 | 0.05 |
| 10. Sodium Formaldehyde Sulfoxylate (1%) | 30.0 | 30.0 |

Procedure:
1. Place (1) and (2) into the reaction flask. Purge with nitrogen.
2. Blend (3), (4), (5), and (6) and add slowly to nitrogen purged (7) and (8), to form a pre-emulsion. Place into an additional funnel equipped with an agitator.
3. Raise batch temperature to 35° C., and remove water bath, so that the flask is air cooled. Add (9) and 5cc of (10).
4. Begin addition of the pre-emulsion at 4 cc per minute with concurrent addition of (10). Exotherm will bring the batch temperature in air to 50–55° C. before all monomer has been added. A peak of 55° C. was reached, at which time a 60° C. bath was placed around the flask, and the reaction brought to completion.
5. Adjust to pH 5.0 with dilute alkali and cool.

Results:

| Solids: | 49% | 50% |
|---|---|---|
| pH: | 5.0 | 5.0 |
| Coagulum: | 0.18% | 0.01% |
| Viscosity: | 17.5 cps. | 20 cps. |
| Turbidity (.01%): | 96 JTU | 125 JTU |
| Surface Tension (1%): | 58.2 dynes/cm | 52.8 dynes/cm |

Both products form clear solutions with ammonia or caustic. Shelf stability of B is over one year at pH 5.0.

EXAMPLE 36

Terpolymer of Vinyl Acetate, 2-Ethylhexyl Acrylate, and Acrylic Acid

Est. Wt.
Ratios: 40/59/1, Example 3–2%

Forms strong, flexible films with excellent water spot resistance.

Recipe:

|  | Parts: |
|---|---|
| 1. Water | 150.0 |
| 2. Example 3 (34%) | 14.6 |
| 3. K$_2$S$_2$O$_8$ | 1.0 |
| 4. Borax | 0.3 |
| 5. Acrylic Acid | 5.0 |
| 6. Vinyl Acetate | 200.0 |
| 7. 2-Ethylhexyl Acrylate | 300.0 |
| 8. Water | 250.0 |
| 9. Example 3 (34%) | 14.6 |
| 10. K$_2$S$_2$O$_8$ | 1.0 |
| 11. Borax | 2.7 |

Procedure:
1. Add (1), (2), (3) and (4) to the reactor flask. Purge with nitrogen, and heat the batch to 70° C.
2. Blend (5), (6), and (7), and add slowly to a solution of (8), (9), (10), and (11), to form a pre-emulsion. Place into an addition funnel.
3. When batch temperature reaches 70° C., add 10% of the preemulsion to the reaction flask. Allow to exotherm. There is usually a 5°–6° C. exotherm. If it does not develop within 15–20 minutes, add a few drops of a solution of sodium metabisulfite.
4. Allow to level off at 75° C. and start adding the preemulsion drop-wise, over a period of 3–3.5 hours. Bath temperature should be at approximately that of the batch (74°–76° C.) throughout the run. When addition is completed, hold at temperature for one hour or until all monomer has reacted.

Results:

| Solids: | 50% |
|---|---|
| pH: | 5.7 |
| Surface Tension: | 58.1 d/cm |
| Turbidity: | 101 JTU |
| Viscosity: | 1290 cps. |

EXAMPLE 37

Acrylic Paint and Paper Type Latex

Monomers: Methyl Methacrylate, Ethyl Acrylate, Methacrylic Acid

Est. Wt.
Ratios: 63/35/2, Example 3, 1.7%, Polystep F-1: 0.3%
Recipe:

|  | Parts: |
|---|---|
| 1. Water (D.I.) | 170.0 |
| 2. Example 3 (26%) | 9.5 |
| 3. (NH$_4$)$_2$S$_2$O$_8$ | 0.75 |
| 4. Methyl Methacrylate | 28.0 |
| 5. Ethyl Acrylate | 15.0 |
| 6. Methacrylic Acid | 1.0 |
| 7. Water (D.I.) | 130.0 |
| 8. Same as Example 3 (26%) | 6.7 |
| 9. (NH$_4$)$_2$S$_2$O$_8$ | 0.25 |
| 10. Polystep F-1 | 0.9 |
| 11. Methyl Methacrylate | 161.0 |
| 12. Ethyl Acrylate | 90.0 |
| 13. Methacrylic Acid | 5.0 |
| 14. Sequestrene NaFe | 0.02 |
| 15. Sodium Hydrosulfite (1%) | 30.0 |
| 16. NaOH (4%) | 10.0 |

Procedure:
1. Add (1), (2), and (3) to the reaction flask. Purge with nitrogen. Add (4), (5), and (6). Mix 15 minutes.

2. Blend (7) and (8). Blend (9), (10), (11) (12), and (13), Add monomers to (7) and (8) to emulsify. Purge with nitrogen. Place into a feed funnel.
3. Set batch temperature at 20° C. Add (14) and start flow of (15). Allow to exotherm 10°–12° C. before starting addition of the pre-emulsion.
4. Add pre-emulsion with concurrent addition of (15) over a 1 to 1.5 hour period. Batch temperature remains below 35° C. throughout the run. When all pre-emulsion is in, heat to 5° C. above batch temperature and hold to remove traces of monomer.
5. Cool to room temperature and add 1.0 N NaOH to desired pH.

Results:

| | |
|---|---|
| Solids: | 44.5% |
| pH: | 8.4 |
| Viscosity: | 17.5 cps. |
| Turbidity (0.01%): | 100 JTU (Jackson Turbidity Units) |
| Surface Tension (1%): | 53.8 d/cm |
| Mechanical Stability: | Excellent |
| Freeze-Thaw Stability: | 5 cycles |
| Coagulum: | 0.13% |

EXAMPLE 38

High Acrylic Acid Styrene Copolymer

Monomers: Styrene, Ethyl Acrylate, Acrylonitrile, Acrylic Acid
Est. Wt.
Ratios: 46.5/30.3/8.2/15.0, Example 3–4%
Recipe:

| | | Parts: |
|---|---|---|
| 1. | Water | 160.0 |
| 2. | Acrylic Acid | 8.0 |
| 3. | Example 3 (34%) | 18.6 |
| 4. | $(NH_4)_2S_2O_8$ | 1.5 |

Recipe:

| | | Parts: |
|---|---|---|
| 5. | Lauryl Thioglycolate | 0.64 |
| 6. | Ethyl Acrylate | 46.6 |
| 7. | Water | 175.0 |
| 8. | Acrylic Acid | 39.6 |
| 9. | Example 3 (34%) | 18.6 |
| 10. | Styrene | 56.0 |
| 11. | Acrylonitrile | 49.7 |
| 12. | Styrene | 92.0 |
| 13. | Acrylonitrile | 26.0 |
| 14. | Tert. Butyl Hydroperoxide | 0.75 |
| 15. | Sequestrene NaFe | 0.002 |
| 16. | Sodium Formaldehyde Sulfoxylate (2%) | 50.0 |

Procedure:
1. Add (1), (2), (3), (4), and (5) to the reaction flask. Flush thoroughly with nitrogen. Add (6).
2. Blend (7), (8), (9), and (14). Flush with nitrogen, and divide into two equal parts.
3. Into PART I add the blend of (10) and (11). Into PART II add the blend of (12) and (13). This will form pre-emulsions of each. (NOTE: The pre-emulsions are not stable and will require constant stirring).
4. Batch temperature and bath may be set at 20°–25° C. at start.
5. Add (15), followed by slow addition of (16). A vigorous exotherm usually occurs within 2–3 minutes. Allow to peak, and start adding PART I, within a 40–45 minute period, continuing to add (16) at a rate to maintain the exotherm.
6. After all of PART I has been added, hold for one-half hour, and start adding PART II, over a one-half hour period. Heat to peak temperature and hold to completion.
7. Cool and add alkali to pH 6–7.

Results:

| | |
|---|---|
| Solids: | 40% |
| Mechanical Stability: | Good |
| Salt Stability: | Excellent |
| Turbidity: | 180 JTU |
| Surface Tension (1%): | 50.5 d/cm |
| Freeze-Thaw Stability: | 5+ cycles |
| Coagulum: | None |

EXAMPLE 39

Sulfonic Acid in Acrylic Paint Type Latex

Monomers: Methyl Methacrylate, Ethyl Acrylate
Est. Wt.
Ratios: 65/35 Example 2, 0.67% (Note that the formula includes no carboxylic acids.)
Recipe:

| | | Parts: |
|---|---|---|
| 1. | Water | 300.0 |
| 2. | Methyl Methacrylate | 30.0 |
| 3. | Example 2 | 1.0 |
| 4. | Mercaptoacetic Acid | 0.2 |
| 5. | Tert. Butyl Hydroperoxide | 1.0 |
| 6. | Sequestrene NaFe | 0.01 |
| 7. | Sodium Formaldehyde Sulfoxylate (2%) | 75.0 |
| 8. | Methyl Methacrylate | 165.0 |
| 9. | Ethyl Acrylate | 105.0 |
| 10. | Example 2 Sulfonic Acid | 1.0 |
| 11. | Tert. Butyl Hydroperoxide | 1.0 |
| 12. | Water | 50.0 |

Procedure:
1. Dissolve (5) in (2). Add (1), (3), and (4) to the reaction flask. Purge with nitrogen.
2. Add (5) in (2) to the reaction flask slowly.
3. Blend (8), (9), and (11) and place into a feed funnel.
4. Dissolve (10) in 50 cc water and place into a feed funnel.
5. Place (7) into a third feed funnel.
6. Adjust batch temperature to 25° C. and add (6) and 10 cc of (7). Allow to exotherm and peak.
7. When the batch temperature has peaked, raise bath temperature 2°–4° C. above the peak and hold for ½ hour. Add 5 cc of (10) in (12), and hold an additional 15 minutes. If temperature has risen above 30° C., cool to 28°–30° C.
8. Start addition of monomer flow together with flow of (7) at a rate to create and maintain an exotherm. After 35 cc monomer blend has been added, stop flow. Allow to peak and slowly raise bath temperature to that of peak, hold 15 minutes. Add 5 cc of dissolved (10). Repeat the above procedure until all of the monomer has been added. Batch temperature should be controlled so that it remains below 50° C. Adjust the incremental addition of dissolved (10) acid so that 5 cc remain for the end of the monomer addition. Total addition period is 6–7 hours.

9. Hold batch temperature at peak after all monomer has been added so as to react any residual. Cool and adjust.

Results:

| | |
|---|---|
| Solids: | 40.1% |
| Coagulum: | 0.1% |
| pH: | 2.2 |
| Mechanical Stability: | Excellent |
| Viscosity: | 15 cps. |
| Surface Tension: | 55.5 d/cm |
| Turbidity (0.01%): | 140 JTU |
| Film has good resistance to heat. | |

EXAMPLE 40

Acrylic Copolymer

Monomers: Methyl Methacrylate, Ethyl Acrylate, Methacrylic Acid
Est.Wt.
Ratios: 86.5/12.5/1.0, Example 3 (2%)
Recipe:

| | | Parts: |
|---|---|---|
| 1. | Water (D.I.) | 400.0 |
| 2. | Example 3 (34%) | 11.7 |
| 3. | K$_2$S$_2$O$_8$ | 1.0 |
| 4. | Example 3 (34%) | 7.3 |
| 5. | Methyl Methacrylate | 350.0 |
| 6. | Ethyl Acrylate | 50.0 |
| 7. | Methyl Methacrylate | 4.0 |
| 8. | Example 3 (34%) | 4.4 |
| 9. | Water (D.I.) | 70.0 |

Procedure:
1. Add (1) and (2) to the reaction flask. Purge thoroughly with nitrogen, and begin heating to 70° C.
2. Blend (5), (6), and (7) and place into a feed funnel.
3. Blend (8) and (9) and place into another feed funnel.
4. When the reactor temperature reaches 70° C., add (3).
5. Add 25% of the monomer blend over a 5–10 minute period, to the reaction flask. Allow to exotherm. React 20 minutes. Add (4). Hold 10 minutes.
6. If the reaction product is still exothermic, start slow addition of remaining monomer. If there is no exotherm, raise the reaction temperature gradually to 82° C. before starting addition. There should be little or no reflux.

When ½ of the total monomer has been added, start adding (8) and (9) at a rate such that all of the monomer and Example 3 solution are in at the same time. Total addition period of all monomer should take about 2 hours. When all monomer has been added, bath temperature should be at 86°–88° C. When the reaction is complete, cool to 25°–30° C., and adjust to pH 9.0.

Results:

| | |
|---|---|
| Solids: | 45% |
| Viscosity: | 17.5 cps. |
| Turbidity (0.01%): | 175 JTU |
| Surface Tension (1%): | 60.5 d/cm |
| Mechanical Stability: | Excellent |
| Polyvalent Ion Stability: | Good |
| Stability to Strong Acid: | Good |

| -continued | |
|---|---|
| Freeze-Thaw Stability: | 5+ cycles |

EXAMPLE 41

A dioxane/SO$_3$ complex is prepared as follows:

| Ingredients: | | Amount in Grams |
|---|---|---|
| 1. | SO$_3$ | 405.0 |
| 2. | Dichloroethane | 200.0 |
| 3. | Dichloroethane | 200.0 |
| 4. | Dioxane | 210.0 |
| 5. | Dichloroethane | 100.0 |
| | | 1115.0 |

1. Blend (1) and (2) and place in feed funnel.
2. Add (3) and (4) to flask.
3. Slowly add (1) and (2) to flask.
4. Add (5) after approximately ½ (1) and (2) are in.
Temperature of bath is −3° to −5° C.
Reaction at about −1° to +2° C.
Product is a paste.
Total Yield: 1100 g (loss occurred on the cover of the stirrer).
Product -
  Color: White and clear
  Total of approx. 5 hr. for feed.

EXAMPLE 42

Using the preceding complex, a portion of the product of Example 1 is sulfonated as follows:

100 grams of dichloroethane are mixed with 575 grams of the product SO$_3$ complex above. To this mixture is added 575 grams of the product of Example 1 gradually. The product is allowed to mix overnight. The next morning 500 grams of H$_2$O were added gradually. The system is mixed well at about 100° C. The resulting mixture is placed in a separation funnel and allowed to separate. The bottom layer is decanted through the bottom. Most of the product bottom layer is organic soluble. Bromine titration showed, with correlation to standard 2.6 double bonds per mole. Solvent dioxane and dichloroethane is removed by evaporation. The resulting product is neutralized with analysis showing the following:

158 g at 61%—96.9 g dry product
303 g at 66%—200 g dry product
94 g NaOH (50%) required—47.0 g dry product In all of the above examples, the reactive surfactant of this invention is incorporated into the product polymer produced by emulsion polymerization.

In each of the Examples 16–42, the polymer produced apparently incorporates the maleate sulfonate contained in the starting mixture. The aqueous phase resulting at the end of each emulsion polymerization appears to contain less than about 0.5 weight percent of starting maleate sulfonate.

EXAMPLES 43–52

The preparative procedure of Examples 1, 2, and 3 is repeated except that, in place of the 6 mol ethylene oxide condensate with nonyl phenol, there is produced and employed the condensate identified in the following Table III. In each case, the acidic sulfonated maleate product, upon analysis, is found to be a corresponding ring monosulfonated maleate half ester terminated product within the scope of formula 2 above. Both the initial sulfonic acid form (where, in formula 2, X is hydrogen) and the subsequently made sodium hydroxide neutralized form (where, in formula 2, X is sodium). Similarly, both the initial sulfonic acid form and the subsequently made sodium hydroxide neutralized form when evaluated for reactivity by the procedure as described above in Example 3 are found to be reactive monomers.

where E and P are ethylene and propylene, respectively, as defined in formula 1 above. The acidic sulfonated maleate product upon analysis is found to be a corresponding ring monosulfonated maleate half ester

TABLE III

| | Starting Material of Formula 1 | | | | |
|---|---|---|---|---|---|
| | [phenoxy poly (alkoxylene)ol] (identification of alkoxylene group) | | | [alkyl phenoxy poly (alkoxylene) ol] | |
| | | | | (identification of alkoxylene group) | |
| Ex. No. | no repeating[1] units | identity of ($R_1O$) | (identification of alkyl group) | no repeating[1] units | identity of ($R_1O$) |
| 43 | — | — | ortho para nonyl | n = 2 | $R_1$ = ethylene |
| 44 | — | — | ortho para nonyl | n = 50 | $R_1$ = ethylene |
| 45 | p = 8<br>q = 1 | $(PO)_p (EO)_q$ | — | — | — |
| 46 | p = 8<br>q = 1<br>r = 8<br>s = 1 | $(PO)_p (EO)_q (PO)_r (EO)_s$ | — | — | — |
| 47 | p = 8<br>q = 1<br>r = 8<br>s = 1<br>u = 8<br>v = 4 | $(PO)_p(EO)_q(PO)_r(EO)_s(PO)_u(EO)_v$ | — | — | — |
| 48 | n = 6 | $R_1$ = ethylene | — | — | — |
| 49 | n = 8 | $R_1$ = ethylene | — | — | — |
| 50 | — | — | ortho, para[2] dodecyl | n = 6.5 | $R_1$ = ethylene |
| 51 | — | — | ortho, para[3] octadecyl | n = 6 | $R_1$ = propylene |
| 52 | — | — | ortho, para[2] dodecyl | n = 9 | $R_1$ = propylene |

[1] value shown is a number average estimated to nearest whole number
[2] the dodecyl chain is branched
[3] the octadecyl chain is normal (unbranched)

EXAMPLE 53

The preparative procedure of Examples 1, 2, and 3 is again repeated, except that here, in place of the 6 mol ethylene oxide condensate with nonyl phenol, there is produced and employed the 6 mol ethylene oxide condensate of a mixture comprised of about 70 weight percent 4 nonyl naphth-1-ol and about 30 weight percent 2 nonyl naphth-1-ol. The acidic sulfonated maleate product upon analysis is found to be a corresponding ring mono-sulfonated maleate half ester terminated product within the scope of formula 2 above. When evaluated for surface tension activity using a DeNuoy Tensionmeter by the procedure of Example 3, this product is found to have a CMC value of at least about $7 \times 10^{-4}$ gm/ml. Similarly, when evaluated for monomer reactivity by the procedure of Example 3, this product is found to be reactive. Similar results are obtained from the sodium salts of this product (produced by neutralization with 10% aqueous NaOH).

EXAMPLE 54

The preparative procedure of Examples 1, 2 and 3 is again repeated, except that here, in place of the 6 mol ethylene oxide condensate with nonyl phenol, there is produced and employed the following alkylene oxide condensate of naphthol:

terminated product within the scope of formula 2 above. When evaluated for surface tension activity using a DeNuoy Tensiometer by the procedure of Example 3, the product is found to have a lower CMC than the corresponding nonionic (non-sulfonated form). Similarly, when evaluated for monomer reactivity by the procedure of Example 3, this product is found to be reactive. Similar results are obtained from the sodium salt of this product (produced by neutralizing with 10% aqueous NaOH).

EXAMPLES 55–75

Using the respective acidic sulfonated maleate half ester terminated aqueous solution products of the above Examples indicated in Table IV below, but employing in place of the NaOH neutralizing solution, bases in 10 weight % aqueous solution as specified in Table IV below, various salts within the scope of formula (2) above are prepared. In each instance, the product demonstrates monomeric surfactant activities under emulsion polymerization conditions similar to those achieved with the respective sodium salts.

TABLE IV

| Ex. No. | Starting acidic sulfonated maleate half ester product Ex. No. | Base |
|---|---|---|
| 55 | 3, part A | $NH_4OH$ |

TABLE IV-continued

| Ex. No. | Starting acidic sulfonated maleate half ester product Ex. No. | Base |
|---|---|---|
| 56 | 3, part A | KOH[1] |
| 57 | 3, part A | triethyl amine |
| 58 | 3, part A | triethanol amine |
| 59 | 3, part A | tetramethylammonium hydroxide |
| 60 | 3, part A | morpholine |
| 61 | 3, part A | monomethylamine |
| 62 | 3, part A | diisopropyl amine |
| 63 | 42 | triethanol amine |
| 64 | 43 | KOH |
| 65 | 44 | triethanol amine |
| 66 | 45 | triethanol amine |
| 67 | 46 | triethanol amine |
| 68 | 49 | triethanol amine |
| 69 | 52 | triethanol amine |
| 70 | 52 | hexanolamine |
| 71 | 53 | KOH |
| 72 | 53 | triethanol amine |
| 73 | 53 | NH$_4$OH |
| 74 | 53 | Pyridine |
| 75 | 53 | disodium phosphate |

[1]only the sulfonic acid potassium salt is formed leaving the maleate carboxyl group unneutralized.

EXAMPLES 76-108

Each of the maleate sulfonates of Examples 42-74 is substituted for maleate sulfonate of Example 3 to prepare a series of aqueous 34% active solutions.

Then each of these solutions is used in Example 38 in place of the Example 3 solution, and emulsion polymerization is conducted as described in Example 38. In each instance, a polymer is produced which apparently incorporates the maleate sulfonate. The aqueous phase resulting at the end of each emulsion polymerization appears to contain less than 0.001 weight percent of starting maleate sulfonate.

Other and further aims, objects, purposes, advantages, uses, and the like for the present invention will be apparent to those skilled in the art from the present specification.

I claim as my invention:

1. A reactive surfactant characterized by the formula

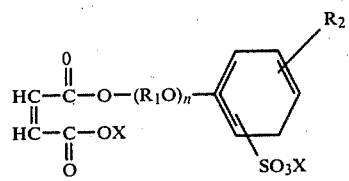

wherein
$R_1$ is selected from the group consisting of ethylene, propylene, and mixtures thereof,
$R_2$ is an alkyl group containing from 8 to 18 carbon atoms,
X is selected from the group consisting of hydrogen, alkali metals, lower alkanal amines, lower alkyl amines, and ammonium, and
n is a positive number of from about 2 to 50.

2. A reactive surfactant of claim 1 wherein X is an alkali metal.

3. A reactive surfactant of claim 1 wherein X is hydrogen.

4. A reactive surfactant of claim 1 wherein X is a lower alkanol amine.

5. A reactive surfactant of claim 1 wherein $R_1$ is ethylene.

6. A reactive surfactant of claim 5 wherein $R_2$ is nonyl.

* * * * *